United States Patent [19]

Umemoto et al.

[11] Patent Number: 4,873,027
[45] Date of Patent: Oct. 10, 1989

[54] FLUOROALKYLARYLIODONUIM COMPOUNDS

[75] Inventors: Teruo Umemoto; Yoshihiko Gotoh, both of Kanagawa, Japan

[73] Assignee: Sagami Chemical Research Center, Tokyo, Japan

[21] Appl. No.: 245,940

[22] Filed: Sep. 19, 1988

Related U.S. Application Data

[60] Division of Ser. No. 148,181, Jan. 27, 1988, abandoned, which is a continuation of Ser. No. 913,591, Oct. 1, 1986, abandoned, which is a continuation of Ser. No. 753,835, Jul. 11, 1985, abandoned.

[30] Foreign Application Priority Data

Jul. 11, 1984 [JP] Japan .............................. 59-142449

[51] Int. Cl.⁴ ..................... C07C 143/02; C07C 19/08
[52] U.S. Cl. ........................................ 562/83; 570/127
[58] Field of Search ...................... 260/505 R, 513 F; 570/127

[56] References Cited

U.S. PATENT DOCUMENTS 4,324,741  4/1982  Umemoto ........................... 260/505
4,786,441  11/1988  Miller .............................. 260/513 F

FOREIGN PATENT DOCUMENTS 0075932  5/1982  Japan ................................. 570/127

*Primary Examiner*—Alan Siegel
*Attorney, Agent, or Firm*—Sughrue, Mion, Zinn, Macpeak & Seas

[57] ABSTRACT

Fluoroalkylaryliodonium compounds having the formula (I):

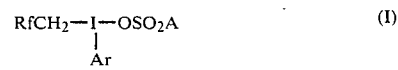

wherein AR, A and Rf are as defined above, are disclosed. The fluoroalkylaryliodonium compounds of the present invention are useful as intermediates for producing N-fluoroalkylanilines or derivatives thereof which are important precursors for fluorine-containing disperse azo dyes having an excellent resistance to light.

2 Claims, No Drawings

FLUOROALKYLARYLIODONUIM COMPOUNDS

This is a division of application Ser. No. 148,181 filed Jan. 27, 1988 now abandoned which is continuation of application Ser. No. 913,591 filed Oct. 1, 1986 now abandoned which is a continuation of application Ser. No 753,835 filed July 11, 1985 now abandoned.

FIELD OF THE INVENTION

This invention relates to a fluoroalkylaryliodonium compound which is useful as an intermediate for producing a fluorine-containing disperse azo dye.

BACKGROUND OF THE INVENTION

The fluoroalkylaryliodonium compounds according to the present invention are represented by the formula (I) below and are useful as intermediates for producing N-fluoroalkylanilines or derivatives thereof which are important precursors for flourine-containing disperse azo dyes having an excellent resistance to light. The N-fluoroalkylanilines and derivatives thereof are described, for example, in Ind. Eng. Chem., 1953, 1730; Kogyo Kagaku Zasshi, 62, 1746 (1959); ibid, 65, 1189 (1962); Nippon Kagaku Kai Shi, 1983, 112; and J. Med. Chem., 16, 1354 (1973), etc.

Conventional methods for producing N-fluoroalkylanilines and derivatives thereof include (1) a method comprising reacting a fluoroalkyl halide with an aniline compound, and (2) a method comprising reacting a fluoroalkyl tosylate, an o-nitrobenzenesulfonate or a trichloromethanesulfonate with an aniline compound, as described in the above-described literature references.

However, the above conventional method (1) is not advantageous since it requires a prolonged reaction time at a high temperature under a pressurized condition in an autoclave, and yet the yield of the desired product is relatively low.

The above conventional method (2) also requires a high reaction temperature, a prolonged reaction time, or the yield of the desired product is relatively low. Moreover, this method tends to form by-products due to the use of polar solvents in the reaction.

As a result of extensive studies for eliminating these disadvantages of the conventional methods for producing N-fluoroalkylanilines or derivatives thereof, the present inventors found that the compounds of this invention can be easily converted into N-fluoroalkylaniline compounds under mild conditions, and completed the present invention.

DETAILED DESCRIPTION OF THE INVENTION

The fluoroalkylaryliodonium compounds according to the present invention are represented by the formula (I):

$$\underset{Ar}{RfCH_2-I^{\oplus}{}^{\ominus}OSO_2A} \qquad (I)$$

wherein Ar represents a substituted or unsubstituted phenyl group wherein the substituent is an alkyl group having 1 to 5 carbon atoms or a halogen atom, A represents an alkyl group having 1 to 10 carbon atoms, an alkoxy group having 1 to 10 carbon atoms, an aryl group, a halogen atom, or a polymer chain, and Rf represents a polyfluoroalkyl group having 1 to 20 carbon atoms or a group of the formula $$\underset{Ar}{ASO_2O-I-CH_2(CF_2)_n,}$$

wherein A and Ar are as defined above, and n is an integer of 1 to 20.

The compounds of the present invention can be prepared by reacting a fluoroalkyliodoso compound represented by the formula (II):

$$Rf'CH_2I(OCOCF_3)_2 \qquad (II)$$

wherein Rf' represents a polyfluoroalkyl group having 1 to 20 carbon atoms or a group of the formula: $(CF_3COO)_2ICH_2(CF_2)_n$ wherein n is an integer of 1 to 20, with an aromatic compound represented by the formula (III):

$$ArH \qquad (III)$$

wherein Ar represents a substituted or unsubstituted phenyl group, and a sulfonic acid represented by the formula (IV):

$$ASO_3H \qquad (IV)$$

wherein A represents an alkyl group having 1 to 10 carbon atoms, an alkoxy group having 1 to 10 carbon atoms, a halogen atom, a hydroxy group or a polymer chain.

The fluoroalkyliodoso compounds represented by the formula (II) can be prepared by reacting a commercially available iodofluoroalkane represented by the formula (V):

$$Rf''CH_2I \qquad (V)$$

wherein Rf'' represents a polyfluoroalkyl group, with trifluoroperacetic acid.

Of the fluoroalkyliodoso compounds of the formula (II) above, the compound wherein Rf' represents $(CF_3COO)_2ICH_2(CF_2)_n-$ can be prepared by reacting an iodofluoroalkane represented by the formula (V) wherein Rf'' represents $ICH_2(CF_2)_n-$ with trifluoroperacetic acid in an amount of at least two mols per mol of the iodofluoroalkane.

The fluoroalkyliodoso compounds represented by the formula (II) used as starting materials for the production of the compounds of this invention include, for example, $CF_3CH_2I(OCOCF_3)_2$, $CF_3CF_2CH_2I(OCOCF_3)_2$, $CF_3(CF_2)_3CH_2I(OCOCF_3)_2$, $(CF_3)_2CFCH_2I(OCOCF_3)_2$, $CF_3(CF_2)_4CH_2I(OCOCF_3)_2$, $CF_3(CF_2)_6CH_2I(OCOCF_3)_2$, $(CF_3)_2CFOCF_2CH_2I(OCOCF_3)_2$, $CF_3CF_2OCF_2CH_2I(OCOCF_3)_2$, $CF_3(CF_2)_7CH_2I(OCOCF_3)_2$, $CF_3(CF_2)_8CH_2I(OCOCF_3)_2$, $CF_3(CF_2)_9CH_2I(OCOCF_3)_2$, $CF_3(CF_2)_{10}CH_2I(OCOCF_3)_2$, $(CF_3)_2CF(CF_2)_6CH_2I(OCOCF_3)_2$, $CF_3(CF_2)_{12}CH_2I(OCOCF_3)_2$, $CF_3(CF_2)_{16}CH_2I(OCOCF_3)_2$, $CF_3(CF_2)_{18}CH_2I(OCOCF_3)_2$, $HCF_2CH_2I(OCOCF_3)_2$, $H(CF_2)_2CH_2I(OCOCF_3)_2$, $H(CF_2)_3CH_2I(OCOCF_3)_2$, $H(CF_2)_4CH_2I(OCOCF_3)_2$, $H(CF_2)_5CH_2I(OCOCF_3)_2$, $H(CF_2)_8CH_2I(OCOCF_3)_2$, $H(CF_2)_{10}CH_2I(OCOCF_3)_2$, $H(CF_2)_{12}CH_2I(OCOCF_3)_2$, $ClCF_2CH_2I(OCOCF_3)_2$, $Cl(CF_2)_2CH_2I(OCOCF_3)_2$, $Cl(CF_2)_3CH_2I(OCOCF_3)_2$, $Cl(CF_2)_4CH_2I(OCOCF_3)_2$, $Cl(CF_2)_6CH_2I(OCOCF_3)_2$, $BrCF_2CH_2I(OCOCF_3)_2$, $Br(CF_2)_2CH_2I(OCOCF_3)_2$, $Br(CF_2)_3CH_2I(OCOCF_3)_2$, $Br(CF_2)_6CH_2I(OCOCF_3)_2$, $Br(CF_2)_{10}CH_2I(OCOCF_3)_2$, $ICF_2CH_2I(OCOCF_3)_2$, $I(CF_2)_2CH_2I(OCOCF_3)_2$, $I(CF_2)_3CH_2I(OCOCF_3)_2$, $I(CF_2)_4CH_2I(OCOCF_3)_2$, $I(CF_2)_5CH_2I(OCOCF_3)_2$, $I(CF_2)_6CH_2I(OCOCF_3)_2$, $I(CF_2)_7CH_2I(OCOCF_3)_2$, $I(CF_2)_8CH_2I(OCOCF_3)_2$, $I(CF_2)_9CH_2I(OCOCF_3)_2$, $I(CF_2)_{10}CH_2I(OCOCF_3)_2$, $CCl_3CF_2CH_2I(OCOCF_3)_2$,

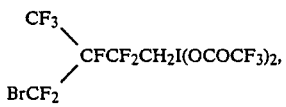

$CF_2ClCFHCF_2CH_2I(OCOCF_3)_2$,
$CF_2BrCF_2ClCH_2I(OCOCF_3)_2$,
$CF_3CHFCF_2CH_2I(OCOCF_3)_2$, $(CF_3COO)_2ICH_2CF_2CH_2I(OCOCF_3)_2$, $(CF_3COO)_2ICH_2(CF_2)_2CH_2I(OCOCF_3)_2$, $(CF_3COO)_2ICH_2(CF_2)_3CH_2I(OCOCF_3)_2$, $(CF_3COO)_2ICH_2(CF_2)_4CH_2I(OCOCF_3)_2$, $(CF_3COO)_2ICH_2(CF_2)_5CH_2I(OCOCF_3)_2$, $(CF_3COO)_2ICH_2(CF_2)_6CH_2I(OCOCF_3)_2$, $(CF_3COO)_2ICH_2(CF_2)_7CH_2I(OCOCF_3)_2$, $(CF_3COO)_2ICH_2(CF_2)_8I(OCOCF_3)_2$, and the like.

Examples of the aromatic compounds represented by the formula (III) include benzene, toluene, fluorobenzene, difluorobenzene, chlorobenzene and the like.

Examples of sulfonic acid represented by the formula (IV) include sulfonic acids having a low molecular weight, such as trifluoromethanesulfonic acid, nonafluorobutanesulfonic acid, perfluorooctanesulfonic acid, difluoromethanesulfonic acid, trichloromethanesulfonic acid, chlorodifluoromethanesulfonic acid, methanesulfonic acid, benzenesulfonic acid, toluenesulfonic acid, nitrobenzenesulfonic acid, dinitrobenzenesulfonic acid, trinitrobenzenesulfonic acid, fluorosulfonic acid, chlorosulfonic acid, monomethyl sulfate, sulfuric acid and the like, and polymers having sulfonic acid groups in the polymer chain thereof, such as polyfluorosulfonic acid resins, polystyrenesulfonic acid resins, etc.

In preparing the compounds of formula (I) of this invention, the reaction between the fluoroalkyliodoso compound of the formula (II) and the compounds of the formulae (III) and (IV) is preferably conducted in a solvent. Examples of solvents which can be used include, for example, methylene chloride, chloroform, carbon tetrachloride, trichlorotrifluoroethane, trichlorofluoromethane, trifluoroacetic acid, trifluoroacetic anhydride, etc. The reaction can be carried out at a temperature in the range of from about $-90°$ C. to about $50°$ C., but is preferably conducted at a temperature in the range of from $-30°$ C. to room temperature (about $15°$ to $30°$ C.) in view of smooth reaction and good yield of the desired product.

In the above reaction, the aromatic compound represented by the formula (III) can be used in an equimolar amount or more, preferably in an equimolar amount to 3 mols, per mol of the fluoroalkyliodoso compound of the formula (II), and the sulfonic acid represented by the formula (IV) can be used in at least equimolar amount, preferably in an equimolar amount, with respect to the fluoroalkyliodoso compound of the formula (II).

The present invention is further illustrated by the following Reference Examples and Examples, but the invention is not limited thereto. The following Reference Examples 1 to 3 illustrate the preparation of starting materials and Reference Examples 4 to 9 illustrate the preparation of N-fluoroalkylanilines from the compounds of this invention.

REFERENCE EXAMPLE 1

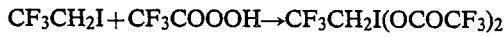

A mixture of 95 ml of trifluoroacetic anhydride and 0.82 ml of trifluoroacetic acid was cooled to 0° C., and 7.56 ml of a 60% aqueous hydrogen peroxide solution was added dropwise to the mixture while stirring, followed by stirring for 10 minutes. To the thus prepared trifluoroperacetic acid solution was added 30 g of 1-iodo-2,2,2-trifluoroethane, and the resulting mixture was stirred for one day while gradually increasing the temperature of the mixture from 0° C. to room temperature (about 25° C.). After completion of the reaction, the solvent was distilled completely under reduced pressure to obtain 60.28 g of 1-bis(trifluoroacetoxy)iodo-2,2,2-trifluoroethane as white crystals. Yield, 97%.

Melting Point: 31°–33° C.

IR Spectrum (neat): 1680 cm$^{-1}$ ($CF_3COO$).

REFERENCE EXAMPLE 2

A mixture of 3 ml of trifluoroacetic anhydride and 0.03 ml of trifluoroacetic acid was cooled to 0° C., and 0.233 ml of a 60% aqueous hydrogen peroxide solution was added dropwise to the mixture while stirring, followed by stirring for 10 minutes. To the thus prepared trifluoroperacetic acid solution was added 2.24 g (4.4 mmol) of 1-iodo-1H,1H-perfluorooctane, and the resulting mixture was stirred overnight at 0° C. After completion of the reaction, the solvent was distilled off completely under reduced pressure to obtain 3.25 g of 1-bis(trifluoroacetoxy)iodo-1H,1H-perfluorooctane as white crystals. Yield, 100%.

IR Spectrum (KBr): 1665 cm$^{-1}$ ($CF_3COO$).

REFERENCE EXAMPLE 3

0.427 ml of a 60% aqueous hydrogen peroxide solution was added dropwise to a mixture of 3.26 ml of trifluoroacetic anhydride and 33 μl of trifluoroacetic acid under ice-cooling while stirring. After stirring for 30 minutes, 5 g of 1-iodo-1H,1H,ωH-perfluoroundecane was added to the mixture, and the temperature of the resulting mixture was allowed to raise gradually to room temperature overnight. The solvent was then distilled off to obtain 6.51 g of 1-bis(trifluoroacetoxy)iodo-1H,1H,ωH-perfluoroundecane as white crystals. Yield, 96%.

Melting Point: 112°–113° C.

EXAMPLE 1

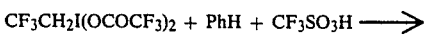

-continued

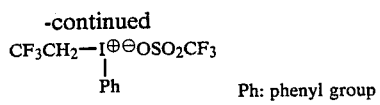

Ph: phenyl group 110 ml of 1,1,2-trichlorotrifluoroethane was added to 30.15 g (69.2 mmol) of 1-bis(trifluoroacetoxy)iodo-2,2,2-trifluoroethane, and, after cooling the mixture to 0° C., 7.4 ml of benzene and 6.1 ml (69.1 mmol) of trifluoromethanesulfonic acid were added to the mixture. After stirring for one day at 0° C., the solvent was distilled off under reduced pressure, and the resulting solid was washed with chloroform to obtain 23.05 g (52.9 mmol) of 2,2,2-trifluoroethylphenyliodonium trifluoromethanesulfonate. Yield, 76%. The result obtained and the physical properties of the product are shown in Tables 1 and 2, respectively.

EXAMPLES 2 TO 9

The reaction was conducted using the procedure and reaction condition similar to those described in Example 1. The results obtained and the physical properties of the resulting compounds are shown in Tables 1 and 2, respectively. In Example 8, the reaction was conducted in the same manner as described in Example 1, except that trifluoromethanesulfonic acid and benzene were used in amounts of 2 mols and 2.4 mols, respectively, per mol of the reactant of formula (II), i.e., $(CF_3COO)_2I—CH_2(CF_2)_3CH_2I(OCOCF_3)_2$.

TABLE 1

$$RfCH_2I(OCOCF_3)_2 + ArH + ASO_3H \longrightarrow RfCH_2-\underset{Ar}{\overset{\oplus}{I}}\ominus OSO_2A$$
$$(II) \quad\quad (III) \quad (IV) \quad\quad\quad\quad (I)$$

| Example No. | (II) | (III) | (IV) | (I) | Yield (%) |
|---|---|---|---|---|---|
| 1 | $CF_3CH_2I(OCOCF_3)_2$ | PhH | $CF_3SO_3H$ | $CF_3CH_2-I^{\oplus}{}^{\ominus}OSO_2CF_3$ / Ph | 76 |
| 2 | " | PhF | " | $CF_3CH_2-I^{\oplus}{}^{\ominus}OSO_2CF_3$ attached to p-F-C$_6$H$_4$ | 72 |
| 3 | $CF_3(CF_2)_2CH_2I(OCOCF_3)_2$ | PhH | " | $CF_3(CF_2)_2CH_2-I^{\oplus}{}^{\ominus}OSO_2CF_3$ / Ph | 70 |
| 4 | $CF_3(CF_2)_6CH_2I(OCOCF_3)_2$ | " | " | $CF_3(CF_2)_6CH_2-I^{\oplus}{}^{\ominus}OSO_2CF_3$ / Ph | 89 |
| 5 | " | " | $FSO_3H$ | $CF_3(CF_2)_6CH_2-I^{\oplus}{}^{\ominus}OSO_2F$ / Ph | 95 |
| 6 | $CF_3(CF_2)_6CH_2I(OCOCF_3)_2$ | PhH | $H_2SO_4$ | $CF_3(CF_2)_6CH_2-I^{\oplus}{}^{\ominus}OSO_3H\cdot H_2O$ / Ph | 49 |
| 7 | $H(CF_2)_{10}CH_2I(OCOCF_3)_2$ | " | $CF_3SO_3H$ | $H(CF_2)_{10}CH_2-I^{\oplus}{}^{\ominus}OSO_2CF_3$ / Ph | 85 |
| 8 | $(CF_3COO)_2ICH_2(CF_2)_3CH_2I(OCOCF_3)_2$ | " | " | $CF_3SO_2O-\underset{Ph}{I}-CH_2(CF_2)_3CH_2-\underset{Ph}{I^{\oplus}}{}^{\ominus}OSO_2CF_3$ | 96 |
| 9 | $CF_3CF_2CH_2I(OCOCF_3)_2$ | " | " | $CF_3CF_2CH_2-I^{\oplus}{}^{\ominus}OSO_2CF_3$ / Ph | 72 |

Note: The symbol "Ph" means a phenyl group.

TABLE 2

| Example No. | m.p. (°C.) | H-NMR Solvent | H-NMR δ | F-NMR CFCl$_3$ Internal Standard Solvent | F-NMR δ | IR Method | IR cm$^{-1}$ | Elemental Analysis (calcd value) C % | H % |
|---|---|---|---|---|---|---|---|---|---|
| 1 | 88–89 (decomp.) | CD$_3$CN | 4.80(q, J = 10 Hz, 2H), 7.40–5.90(m, 3H), 8.00–8.30 (m, 2H) | CD$_3$CN | 61.5(t, J = 10 Hz, 3F), 77.9 (s, 3F) | KBr | 3060, 3040, 2970 (CH), 1565, 1475 (aromatic ring), 1275, 1245, 1170 (CF) | 25.03 (24.79 | 1.51 (1.62) |
| 2 | 101–103 | | 4.77(q, J = 10 Hz, | | 61.1(t, J = 10 Hz, | | 3050, 2980 (CH), | | |

TABLE 2-continued

| Example No. | m.p. (°C.) | H-NMR Solvent | H-NMR δ | F-NMR Solvent | F-NMR CFCl$_3$ Internal Standard | IR Method | IR cm$^{-1}$ | Elemental Analysis (calcd value) C % | H % |
|---|---|---|---|---|---|---|---|---|---|
| | | CD$_3$CN | 2H), 7.33 (dd, J = 9, 9 Hz, 2H), 8.20 (dd, J = 9, 4.5 Hz, 2H) | CD$_3$CN | 3F), 77.5(s, 3F), 102.8(bs, 1F) | KBr | 1583, 1490 (aromatic ring), 1260, 1180 (CF) | 23.68 (23.81) | 1.16 (1.33) |
| 3 | 133 (decomp.) | CD$_3$CN | 4.80(t, J = 18 Hz, 2H), 7.60–7.95 (m, 3H), 8.10–8.30(m, 2H) | CD$_3$CN | 80.8(s, 3F), 82.6(t, J = 15 Hz, 3F), 107.2(m, 2F), 128.1(s, 2F) | KBr | 3070, 3050 (CH), 1570, 1480 (aromatic ring), 1350, 11250, 1180 (CF) | 24.39 (24.64) | 1.24 (1.32) |
| 4 | 142–143 (decomp.) | CD$_3$CN | 4.83(t, J = 18 Hz, 2H), 7.40–7.80 (m, 3H), 8.05–8.25(m, 2H) | CD$_3$CN | 78.0(s, 3F), 80.6(s, 3F), 102.8(m, 2F), 120.8 (m, 8F), 124.9 (m, 2F) | KBr | 3070, 3000 (CH), 1480 (aromatic ring), 1370, 1250, 1100 (CF) | 24.38 (24.48) | 0.85 (0.96) |
| 5 | 107 (decomp.) | CD$_3$CN | 4.83(t, J = 18 Hz, 2H), 7.40–7.90 (m, 3H), 8.10–8.30(m, 2H) | CD$_3$CN | −38.5(s, 1F, —OSO$_2$F), 80.3 (t, J = 10 Hz, 3F), 103.2 (m, 2F), 120.8 (m, 6F), 122.0 (m, 2F), 125.5 (m, 2F) | KBr | 3070, 3000 (CH), 1480 (aromatic ring), 1370, 1280, 1220, 1140 (CF) | 24.24 (24.51) | 0.96 (1.03) |
| 6 | 90–91 (decomp.) | Acetone-$d_6$ | 5.16(t, J = 18 Hz, 2H), 7.40–7.80 (m, 3H), 8.20–8.40 (m, 2H) | DMSO-$d_6$ | 80.0(t, J = 10 Hz, 3F), 120.5(m, 2F), 121.6(m, 4F), 122.2(m, 2F), 122.8(m, 2F), 125.6(m, 2F) | KBr | 3450 (OH), 3080, 3050 (CH), 1580, 1480 (aromatic ring), 1370, 1320, 1210, 1150 (CF) | 23.73 (23.95) | 1.25 (1.44) |
| 7 | 157–158 | CD$_3$CN | 4.92(t, J = 18 Hz, 2H), 6.52(tt, J = 51.0, 4.8 Hz, 1H), 7.5–8.32(m, 5H) | CD$_3$CN | 78.11(s, 3F), 103.1(bs, 2F), 120.2–123.1 (m, 14F), 128.7(bs, 2F), 137.8(d, J = 51.0 Hz 2F) | KBr | 3090, 3020(CH), 1480 (aromatic ring), 1260, 1210, 1155 (CF) | 24.80 (24.90) | 0.89 (0.93) |
| 8 | 113–114 (decomp.) | CD$_3$CN | 4.80(t, J = 18 Hz, 4H), 7.40–7.90 (m, 6H), 8.00–8.20 (m, 4H) | CD$_3$CN | 78.0(s, 6F), 102.6(m, 4F), 120.9(s, 2F) | KBr | 3080 (CH), 1580, 1480 (aromatic ring), 1260, 1180 (CF) | 25.63 (25.81) | 1.60 (1.60) |
| 9 | 130 (decomp.) | Acetone-$d_6$ | 5.20(t, J = 18 Hz, 2H), 7.46–7.96 (m, 3H), 8.26–8.50(m, 2H) | Acetone-$d_6$ | 77.3(s, 3F), 82.7(s, 3F), 106.5(t, J =, 18 Hz, 2F) | KBr | 3040, 2980 (CH), 1570, 1480 (aromatic ring), 1220, 1180 (CF) | 24.78 (24.70) | 1.19 (1.45) |

EXAMPLE 10

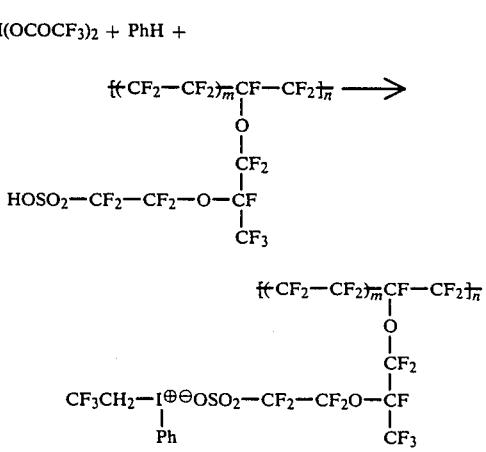

Nafion Powder 511 (produced by E. I. DuPont) having the following structure:

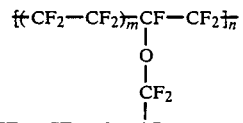

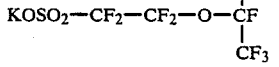

wherein m is 5 to 13.5; n is about 1000; and a softening point: 220° C.) was treated with 3N aqueous hydrochloric acid solution at 60° C. to 70° C. overnight to convert the sulfonate salt to an acid form. The acid concentration of the resulting acid-treated polymer was determined by titration and found to be 0.87 mmol/g. A mixture of 2.30 g of the fluorocarbonsulfonic acid polymer thus obtained, 0.87 g of 1-bis(trifluoroacetoxy)iodo-2,2,2-trifluoroethane, 0.213 ml of benzene and 6 ml of trifluoroacetic acid was stirred for one day while increasing the temperature from 0° C. to room temperature and, thereafter, the mixture was stirred at room temperature for 3 days. The resulting polymer was collected by filtration, washed with trichlorotrifluoroethane and dried under reduced pressure at room temperature to obtain 2.84 g of the product. The infrared absorption spectrum (by KBr method) of the product showed absorptions based on the terminal structure

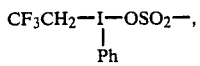

i.e., 3070 (shoulder, aromatic ring CH), 3050 (aromatic ring CH), 2990 (saturated CH), 1570 and 1480 (both aromatic ring), 1435, 1410, 1050, 905, 810, 740 cm$^{-1}$.

REFERENCE EXAMPLE 4

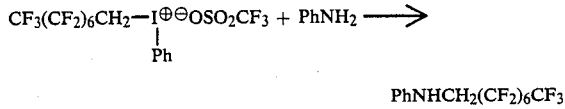

PhNHCH$_2$(CF$_2$)$_6$CF$_3$

A mixture of 250 mg (0.34 mmol) of (1H,1H-perfluorooctyl)phenyliodonium trifluoromethanesulfonate, 63.3 mg (0.68 mmol) of aniline and 5 ml of methylene chloride was stirred at room temperature for 1.5 hour. Then, an aqueous sodium bicarbonate solution was added to the mixture, and the mixture was extracted with diethyl ether. The resulting product was purified by silica gel thin layer chromatography to obtain 162 mg of N-(1H,1H-perfluorooctyl)aniline. Yield, 100%.

Melting Point: 43°–44° C.

IR Spectrum (KBr): 3450 (NH), 1610 and 1520 (both aromatic ring), 1260–1150 cm$^{-1}$ (CF).

Elemental Analysis for C$_{14}$H$_8$F$_{15}$N: Found: (%): C, 35.34; H, 1.69; N, 2.94. Calcd (%): C, 35.38; H, 1.78; N, 2.95.

REFERENCE EXAMPLE 5

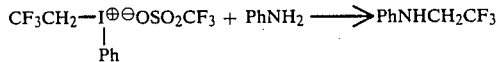

250 mg (0.573 mmol) of (2,2,2-trifluoroethyl)phenyliodonium trifluoromethanesulfonate, 107 mg (1.15 mmol) of aniline and 5 ml of methylene chloride were reacted and worked up in the same manner as described in Reference Example 4 to obtain 91.1 mg of N-(2,2,2-trifluoroethyl)aniline as an oily substance. Yield, 92%.

IR Spectrum (neat): 3425 cm$^{-1}$ (NH).

$^{19}$F-NMR (in CDCl$_3$; internal standard, CFCl$_3$): 72.5 ppm (t, J=8.5 Hz, CF$_3$).

$^1$H-NMR (in CDCl$_3$): δ3.63 (q, J=8.5 Hz, CH$_2$), 6.48–7.30 (m, 5H, aromatic ring H).

REFERENCE EXAMPLE 6

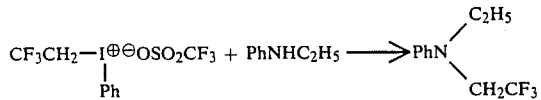

203 mg (0.465 mmol) of (2,2,2-trifluoroethyl)phenyliodonium trifluoromethanesulfonate, 113 mg (0.931 mmol) of N-ethylaniline and 5 ml of methylene chloride were treated and worked up in the same manner as described in Reference Example 4 to obtain 92.6 mg of N-ethyl-N-(2,2,2-trifluoroethyl)aniline as an oily substance. Yield, 98%.

·F-NMR (in CDCl$_3$, internal standard: CFCl$_3$): 70.5 ppm (t, J=8.5 Hz, CF$_3$).

$^1$H-NMR (in CDCl$_3$): δ1.16 (t, J=6.2 Hz, CH$_3$), 3.43 (q, J=6.2 Hz, CH$_2$), 3.77 (q, J=8.5 Hz, CH$_2$CF$_3$), 6.60–7.36 (m, 5H, aromatic ring H).

REFERENCE EXAMPLE 7

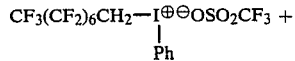

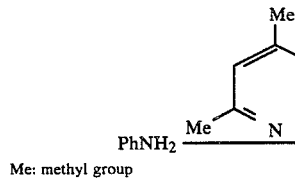

Me: methyl group

A mixture of 251.5 mg (0.34 mmol) of (1H,1H-perfluorooctyl)phenyliodonium trifluoromethanesulfonate, 32 mg (0.34 mmol) of aniline, 42 mg (0.34 mmol) of 2,4,6-collidine and 5 ml of methylene chloride was stirred at room temperature for 1.5 hour. The mixture was then worked up in the same manner as described in Reference Example 4 to obtain 157 mg of N-(1H,1H-perfluorooctyl)aniline. Yield, 97%. Physical properties of the product are shown in Reference Example 4.

REFERENCE EXAMPLE 8

CF$_3$—CH$_2$—I$^\oplus$$^\ominus$OSO$_2$CF$_3$ +

| Ph

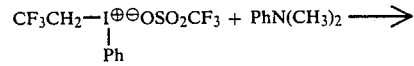

310 mg (1.49 mmol) of 2,6-di-tert-butyl-4-methylpyridine was added to a solution of 654 mg (1.49 mmol) of (2,2,2-trifluoroethyl)phenyliodonium trifluoromethanesulfonate in 5 ml of methylene chloride in an argon atmosphere at room temperature, and then 46 mg (1.49 mmol of aniline was added to the mixture. After stirring for 2 hours at room temperature for 2 hours, the mixture was worked up in the same manner as described in Reference Example 4 to obtain 119 mg (94%) of N,N-bis(2,2,2-trifluoroethyl)aniline.

$^{19}$F-NMR (in CDCl$_3$, internal standard: CFCl$_3$): 69.8 ppm (t, J=9 Hz).

$^1$H-NMR (in CDCl$_3$): δ3.98 (q, J=9 Hz, 2×CH$_2$), 6.70–7.02 (m, 3H), 7.10–7.40 (m, 2H).

REFERENCE EXAMPLE 9

CF$_3$CH$_2$—I$^\oplus$$^\ominus$OSO$_2$CF$_3$ + PhN(CH$_3$)$_2$ ⟶

| Ph

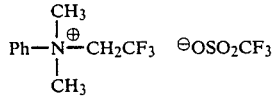

61 mg (0.50 mmol) of N,N-dimethylaniline was added to a solution of 218 mg (0.50 mmol) of (2,2,2-trifluoroethyl)phenyliodonium trifluoromethanesulfonate in an argon atmosphere at room temperature, and the mixture was stirred for 30 minutes. After completion of the reaction, the reaction mixture was concentrated and purified by silica gel thin-layer chromatography to obtain 157 mg (89%) of N,N-dimethyl-N-phenyl-N-2,2,2-trifluoroethylammonium trifluoromethanesulfonate.

Melting Point: 82°–84° C.

$^{19}$F-NMR (in deuteroacetone, internal standard: CFCl$_3$): 62.3 ppm (t, J=9 Hz, CF$_3$CH$_2$), 78.0 (s, CF$_3$).

$^1$H-NMR (in deuteroacetone): δ4.10 (s, CH$_3$), 5.25 (q, J=9 Hz, CH$_2$CF$_3$), 7.56–7.83 (m, 3H), 8.06–8.26 (m, 2H).

Mass Spectrum (m/e): 204 (M$^+$—OSO$_2$CF$_3$).

While the invention has been described in detail and with reference to specific embodiments thereof, it will be apparent to those skilled in the art that various changes and modifications can be made therein without departing the spirit and scope thereof.

What is claimed is:

1. A fluoroalkyliodonium compounds represented by the formula (I):

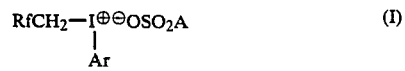

wherein Ar represents a substituted or unsubstituted phenyl group wherein the substituent is an alkyl group having 1 to 5 carbon atoms or a halogen atom, A represents a trifluoromethyl group or a fluorine atom, and Rf represents a polyfluoroalkyl group having 1 to 20 carbon atoms or a group of the formula

wherein A and Ar are as defined above, and n is an integer of 1 to 20.

2. A fluoroaklylaryliodium compound of claim 1, wherein A is trifluoromethane.

* * * * *